United States Patent [19]

Amelse et al.

[11] Patent Number: 4,962,258

[45] Date of Patent: Oct. 9, 1990

[54] LIQUID-PHASE XYLENE ISOMERIZATION

[75] Inventors: Jeffrey A. Amelse, Batavia; John A. Donohue, Elmhurst; Nancy A. Kutz, Wheaton; Judith B. Melville, Downers Grove; Brian L. Slusar, Winfield, all of Ill.

[73] Assignee: Amoco Corporation, Chicago, Ill.

[21] Appl. No.: 285,105

[22] Filed: Dec. 15, 1988

[51] Int. Cl.$^5$ .............................................. C07C 5/22
[52] U.S. Cl. ...................................... 585/480; 585/481
[58] Field of Search ................................ 585/480, 481

[56] References Cited

U.S. PATENT DOCUMENTS 4,435,608  3/1984  Koetsier et al. ...................... 585/480
4,482,774  11/1984 Koetsier ............................... 585/481
4,762,957  8/1988  Sachtler et al. ...................... 585/481

Primary Examiner—Curtis R. Davis
Attorney, Agent, or Firm—Reed F. Riley; William H. Magidson; Ralph C. Medhurst

[57] ABSTRACT

Gallium-containing, crystalline silicate molecular sieves in which substantially all of the gallium occupies molecular sieve lattice positions or is intimately associated with the crystal lattice of the silicate sieve when composited into a silica matrix are shown to form catalyst compositions having superior properties for the catalytic, liquid-phase isomerization of a xylene-containing stream containing a minor amount of ethylbenzene to a product mixture rich in paraxylene.

6 Claims, No Drawings

LIQUID-PHASE XYLENE ISOMERIZATION

BACKGROUND OF THE INVENTION

This invention relates to a liquid-phase process for catalytically isomerizing a xylene stream containing a minor amount of ethylbenzene to a mixture rich in para-xylene, and, more particularly, to a liquid-phase process to catalytically isomerize a xylene stream containing a minor amount of ethylbenzene to a product mixture rich in para-xylene over a silica-supported, gallium-containing, crystalline silicate molecular sieve in which substantially all of the gallium is in molecular sieve lattice positions or is intimately associated with the silicate sieve crystal lattice.

Typically, p-xylene is derived from mixtures of $C_8$ aromatics separated from such raw materials as petroleum naphthas, particularly reformates, usually by isomerization followed by, for example, lower-temperature crystallization of the p-xylene with recycle of the crystallizer liquid phase to the isomerizer. Principal raw materials are catalytically reformed naphthas and petroleum distillates. The fractions from these sources that contain the $C_8$ aromatics vary quite widely in composition but will usually contain 10 to 35 weight percent ethylbenzene and up to about 10 weight percent primarily $C_9$ paraffins and naphthenes with the remainder being primarily xylenes divided approximately 50 weight percent meta, and 25 percent each of the ortho and para isomers. Feeds that do not have the primarily $C_9$ paraffins and naphthenes removed by extraction are termed "unextracted" xylene feeds.

The ethylbenzene in a xylene mixture is very difficult to separate from the other components due to similar volatility, and, if it can be converted during isomerization to products more readily separated from the xylenes, build up of ethylbenzene in the recycle loop is prevented and process economics are greatly improved. The primarily $C_9$ paraffins and naphthenes present in unextracted feeds unless removed also build up in the recycle loop and are usually extracted prior to isomerization as most commercial isomerization processes do not provide a catalyst which effectively converts them to easily separable-by-distillation products.

The xylene isomerization process is an important step in the eventual production of polyester based upon terephthalic acid. The p-xylene isomerization product is oxidized to terephthalic acid, conveniently by a cobalt ion/acetic acid liquid-phase oxidation, which is a raw material for the production of polyethylene terephthalate.

Xylene isomerization is commercially performed in the vapor phase using a catalyst that exhibits catalytic activity for both the isomerization of xylenes and the conversion of at least the ethylbenzene impurity present in the feedstock as mentioned above. Isomerization in the liquid phase, however, is preferred, but a number of problems, mainly catalyst lifetime, arising in liquid-phase isomerization have led to the vapor-phase process being the commercial choice.

Isomerization of xylenes in the liquid phase has been a subject of study by a number of workers. See for example, U.S. Pat. Nos. 3,777,400; 3,856,871; 4,268,420; and 4,269,813; Japanese Kokai 57-32233 (1982); and a 1972 article in "Hydrocarbon Processing" at p. 85 by P. Grandio, F. H. Schneider, A. B. Schwartz and J. J. Wise. In these reports, the primary reaction observed was isomerization of xylenes, even in the presence of ethylbenzene and other impurities. In fact, molecules such as toluene and ethylbenzene were sometimes added to the process to improve the selectivity of the catalysts toward isomerization (rather than disproportionation) of the xylenes. Most of the catalysts which were employed in the above works contained zeolites of the large-pore type, e.g., faujasite-type zeolites or mordenite.

U.S. Pat. No. 3,856,879 is an early report of the use of shape-selective, molecular-sieve-containing catalysts for the isomerization of xylenes and the conversion of ethylbenzene in the liquid phase. The aluminosilicate zeolites ZSM-5, ZSM-12, and ZSM-21 are recommended for use in this process. Although by-product distributions are not reported in the patent, the xylene feed is said to be isomerized to its equilibrium isomer concentrations and the ethylbenzene converted via the transalkylation and disproportionation mechanisms. A catalyst containing the aluminosilicate molecular sieve, ZSM-5, was claimed to exhibit no deactivation, even in the absence of hydrogen. However, other unpublished results show that, contrary to the teaching of this patent, a ZSM-5 type sieve (35 weight percent on alumina) catalyst composition exhibits rapid deactivation and poor selectivity.

Gallium-containing molecular sieve catalyst compositions are taught in a number of publications for hydrocarbon conversions; in particular, U.S.S.N. 202,210 filed on June 3, 1988, now U.S. Pat. No. 4,812,536, teaches the use of such materials with added magnesium compound for the para-ethylation of toluene.

Now catalyst compositions based upon gallium silicate molecular sieves have been found which exhibit for the liquid-phase isomerization of xylene streams containing a minor amount of ethylbenzene improved catalyst lifetimes at good selectivities as measured by (1) considerably better overall selectivity as measured by the ratio of percent total ethylbenzene conversion to percent xylene loss, and (2) a lower deactivation rate (longer lifetime) than the usual commercial aluminosilicates and borosilicates when used in liquid-phase xylene isomerization.

BRIEF DESCRIPTION OF THE INVENTION

The invention described herein is an improved process to catalytically isomerize in the liquid phase a stream containing a major amount of one or more xylenes and a minor amount of ethylbenzene to a product rich in paraxylene, the improvement comprising isomerizing said stream under isomerization conditions over a catalyst composition which contains about 10 to about 80 weight percent, based upon the total weight of said catalyst composition, of a gallium-containing, crystalline silicate molecular sieve incorporated into about 20 to about 90 weight percent, based upon the total weight of said catalyst composition, of a silica matrix, said sieve containing about 0.5 to about eight weight percent gallium, calculated as the metal, substantially all of said gallium either occupies molecular sieve lattice positions or is intimately associated with the crystal lattice of said crystalline silicate molecular sieve, and said sieve providing an x-ray pattern comprising the following x-ray diffraction lines and strengths:

| Interplanar Spacing d, Å | Assigned Strength | Interplanar Spacing d, Å | Assigned Strength |
|---|---|---|---|
| 11.14 ± 0.5 | VS | 3.82 ± 0.1 | M |
| 10.05 ± 0.4 | S | 3.75 ± 0.1 | W |
| 6.36 ± 0.2 | W | 3.72 ± 0.1 | M |
| 5.99 ± 0.15 | W | 3.64 ± 0.1 | W |
| 5.57 ± 0.15 | W | 3.34 ± 0.05 | W |
| 3.85 ± 0.1 | S | 2.98 ± 0.04 | W |

DETAILED DESCRIPTION OF THE INVENTION

The gallium silicate crystalline molecular sieves used in this invention are characterized by the representative X-ray pattern listed in Table 1 below and by the composition formula:

$$0.9 \pm 0.2\ M_{2/n}O:Ga_2O_3:ySiO_2:zH_2O$$

wherein M is at least one cation, n is the valence of the cation, y is between about 24 and about 600, and z is between 0 and about 160. It is believed that substantially all of the gallium content of the sieves occupies molecular sieve lattice positions or is intimately associated with the molecular sieve crystal lattice, existing in the latter case as individual or small clusters of gallium ions in the sieve pores. Attempts to remove the gallium from the gallium silicate sieves by washing or exchanging with ammonium ion removes little of the gallium and therefore, the gallium content is believed firmly anchored in the main to the silicate lattice.

TABLE 1

| d-Spacing Å (1) | Assigned Strength (2) | d-Spacing Å (1) | Assigned Strength (2) |
|---|---|---|---|
| 11.14 ± 0.5 | VS | 3.82 ± 0.1 | M |
| 10.05 ± 0.4 | S | 3.75 ± 0.1 | W |
| 6.36 ± 0.2 | W | 3.72 ± 0.1 | M |
| 5.99 ± 0.15 | W | 3.64 ± 0.1 | W |
| 5.57 ± 0.15 | W | 3.34 ± 0.05 | W |
| 3.85 ± 0.1 | S | 2.98 ± 0.04 | W |

(1) Copper K alpha radiation
(2) VW (<5) = very weak; W (5-20) = weak; M (20-40) = medium; S (40-80) = strong; VS (80-100) = very strong The gallium silicate molecular sieve useful in this invention can be prepared by crystallizing an aqueous mixture, at a controlled pH, of a base, a gallium ionaffording material, an oxide of silicon, and an organic template compound, and, optionally, a gallium mineralizing agent such as 2,4-pentanedione.

Typically, the mol ratios of the various reactants can be varied to produce the crystalline gallium silicates of this invention. Specifically, the mol ratios of the initial reactant concentrations are indicated in Table 2 below:

TABLE 2

|  | Broad | Preferred | Most Preferred |
|---|---|---|---|
| $SiO_2/Ga_2O_3$ | 24-600 | 24-200 | 32-100 |
| Base/$SiO_2$ | 0.05-5 | 0.01-1 | 0.1-0.5 |
| $H_2O/SiO_2$ | 5-80 | 10-50 | 20-40 |
| Template/$SiO_2$ | 0-1 | 0.01-0.2 | 0.02-0.1 |
| Mineralizer/$Ga_2O_3$ | 0-100 | 5-60 | 5-30 |

By regulation of the quantity of gallium (represented as $Ga_2O_3$) in the reaction mixture, it is possible to vary the $SiO_2O_3$ molar ratio in the final product. In general, it is desirable to have the gallium content of the gallium silicate sieve of this invention between about 0.5 and about 8 percent by weight of gallium. More preferably, the amount of gallium should be between about 1 and about 8 weight percent gallium and, most preferably, between about 2 and about 6.5 weight percent of gallium. Too much gallium in the reaction mixture appears to reduce the sieve crystallinity which reduces the catalytic usefulness of the sieve. Too little gallium makes the sieve ineffective for the purposes of this invention.

More specifically, the material useful in the present invention can be prepared by mixing a base, a gallium ion-affording substance, optionally a gallium mineralizing agent, an oxide of silicon, and an organic template compound in water (preferably distilled or deionized). The order of addition usually is not critical although a typical procedure is to dissolve the organic base and the gallium ion-affording substance in water and then add the template compound. Generally, the silicon oxide compound is added with mixing, the final pH is reached by addition of the base, and the resulting slurry is transferred to a closed crystallization vessel for a suitable time. After crystallization, the resulting crystalline product can be filtered, washed with water, dried, and calcined.

During preparation, acidic conditions should be avoided. Advantageously, the pH of the reaction mixture falls within the range of about 9.0 to about 13.0; more preferably between about 10.0 and about 12.0 and most preferably between about 10.3 and 11.3.

Examples of oxides of silicon useful in this invention include silicic acid, sodium silicate, tetraalkyl silicates, and Ludox, a stabilized polymer of silicic acid manufactured by E. I. DuPont de Nemours & Co. Typically, the oxide of gallium source is a water-soluble gallium compound such as gallium nitrate or gallium acetate or another gallium compound, the anion of which is easily removed during sieve calcination prior to use. Water-insoluble gallium compounds such as the oxide can be used as well. Gallium nitrate is the preferred source of gallium.

Gallium mineralizing agents which are used optionally include ketones, alcohols or organic esters, such as ethanol, butanol, ethylene glycol, methyl ethyl ketone, or 2,4-pentanedione. The latter compound is preferred.

Cations useful in formation of the gallium silicate sieves include the sodium ion and the ammonium ion. The sieves also can be prepared directly in the hydrogen form with an organic base such as ethylenediamine. The hydrogen form of the gallium silicate sieve is preferred.

Organic templates useful in preparing the crystalline gallium silicate include alkylammonium cations or precursors thereof such as tetraalkylammonium compounds, especially tetrapropylammonium compounds. A useful organic template is tetra-n-propylammonium bromide. Diamines, such as hexamethylenediamine, can be used.

The crystalline gallium silicate molecular sieve can be prepared by crystallizing a mixture of sources for an oxide of silicon, an oxide of gallium, optionally a mineralizing agent such as 2,4-pentanedione, an alkylammonium compound, and a base such as sodium hydroxide, ammonium hydroxide or ethylenediamine such that the initial reactant molar ratios of water to silica range from about 5 to about 80, preferably from about 10 to about 50 and most preferably from about 20 to about 40. In addition, preferable molar ratios for initial reactant silica to oxide of gallium range from about 4 to about 200, more preferably from about 10 to about 150 and most preferably from about 20 to about 100. If used, the molar ratio of 2,4-pentanedione to gallium should be below about 50. More preferably, the molar ratio lies between about 5 and about 40 and, most preferably about 10 and about 30. The molar ratio of base to silicon oxide should be above about 0.5, typically below about 5, preferably between about 0.05 and about 1.0 and most preferably between about 0.1 and about 0.5. The molar ratio of alkylammonium compound, such as tetra-n-propylammonium bromide, to silicon oxide can range from 0 to about 1 or above, typically above about 0.005, preferably about 0.01 to about 0.2, most preferably about 0.02 to about 0.1.

The resulting slurry is transferred to a closed crystallization vessel and reacted usually at a pressure at least the vapor pressure of water for a time sufficient to permit crystallization which usually is about 1 to about 25 days, typically is about 1 to about 10 days and preferably is about 1 to about 8 days, at a temperature ranging from about 100° C. to about 250° C., preferably about 125° C. to about 200° C. The crystallizing material can be stirred or agitated as in a rocker bomb. Preferably, the crystallization temperature is maintained below the decomposition temperature of the organic template compound. Especially preferred conditions are crystalizing at about 150° C. for about 3 to about 8 days. Samples of material can be removed during crystallization to check the degree of crystallization and determine the optimum crystallization time.

The crystalline material formed can be separated and recovered by well-known means such as filtration with aqueous washing. This material can be mildly dried for anywhere from a few hours to a few days at varying temperatures, typically about 50° C. to about 225° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, the mildly dried product is calcined at temperatures ranging from about 260° C. to about 850° C. and preferably from about 425° C. to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 4 to about 16 hours and is then calcined in air in a manner such that the temperature rise does not exceed 125° C. per hour until a temperature of about 540° C. is reached. Calcination at this temperature usually is continued for about 4 to about 12 hours. The gallium silicate sieves thus made generally have a surface area greater than about 300 sq. meters per gram as measured by the BET procedure.

Alternatively, the gallium-containing crystalline, silicate molecular sieve can be made by treating a crystalline borosilicate molecular sieve with a relatively volatile, gallium compound such as gallium chloride in the vapor phase at elevated temperature until active gallium is deposited in the sieve. After cooling the molecular sieve is washed repeatedly with distilled water to remove chloride and boron.

The gallium silicate sieve useful in this invention is admixed with or incorporated within various binders or matrix materials depending upon the intended process use. The crystalline gallium silicates are combined with active or inactive materials, synthetic or naturally occurring zeolites, as well as inorganic or organic materials which would be useful for binding the gallium silicate. Well-known materials include silica, silica-alumina, alumina, magnesia, titania, zirconia, alumina sols, hydrated aluminas, clays such as bentonite or kaolin, or other binders well-known in the art. Typically, the gallium silicate is incorporated within a matrix material by blending with a sol of the matrix material and gelling the resulting mixture or slurrying the sieve with the matrix material and drying. Also, solid particles of the gallium silicate and matrix material can be physically admixed. Typically, such gallium compositions can be pelletized or extruded into useful shapes. The crystalline gallium silicate content can vary anywhere from a few up to 100 weight percent of the total composition. Catalytic compositions can contain about 0.1 weight percent to about 100 weight percent crystalline gallium silicate material and preferably contain about 10 weight percent to about 95 weight percent of such material and most preferably contain about 20 weight percent to about 80 weight percent of such material.

Silica-supported gallium silicate catalyst compositions which are preferred can be made by dry mixing the gallium silicate sieve with a silica source such as Cab-O-Sil, adding water and stirring. The resulting solid is then dried below about 200° C. and finally calcined between about 350° C. and 700° C.

The preferred molecular sieves that contain gallium should have framework topology designations of MFI, MEL, FER, TON, EUO, or MTT, as proposed in W. H. Meier, and D. H. Olson, "Atlas of Zeolite Structure Types," Structure Commission of the International Zeolite Association (1978) and A. C. Rohrman, Jr., R. B. LaPierre, J. L. Schlenker, J. D. Wood, E. W. Valyocsik, M. K. Rubin, J. B. Higgins, and W. J. Rohrbaugh, Zeolites, 5, 353 (1985), and/or having framework topologies similar to ZSM-5 (U.S. Pat. No. 3,702,886), ZSM-11 (U.S. Pat. No. 3,709,971), ZSM-22, ZSM-23, ZSM-48, ZSM-50, theta-1, ferrierite, Nu-10, KZ-2, ISI-1, EU-1, EU-2, ZBM-30, EU-11, ISI-4, KZ-1, TPZ-3, and AMS-1B (U.S. Pat. Nos. 4,268,420; 4,269,813; 4,285,919 and published European Application 68796).

The preferred molecular sieve for use herein is a gallium-containing, crystalline silicate molecular sieve in which the gallium occupies molecular sieve lattice positions or is intimately associated with the silicate crystal lattice, existing in the latter case as individual or small clusters of gallium ions in the sieve pores. Attempts to remove the gallium from the gallium-containing silicate molecular sieves by washing or exchanging with ammonium ion removes little of the gallium and therefore the gallium is believed firmly anchored in the main to the silicate lattice.

Process conditions used for the conversion of xylenes and ethylbenzene are partly dependent on the activity of the catalyst composition used. The process temperature can be from about 350° to about 650° F., or more preferably from about 500° to about 650° F.; most preferably the temperature range should be from about 550° to about 650° F. The upper temperature of the range is chosen so that the hydrocarbon feed to the process will remain in the liquid phase. Thus, the upper temperature limit is the critical temperature for the particular hydrocarbon mixture present in the reactor. The lower temperature limit is dependent on the activity of the catalyst composition and varies somewhat depending on the particular catalyst composition used.

The total pressure used in the process should be high enough to maintain the hydrocarbon feed to the reactor in the liquid phase. There is no upper limit for the total pressure useful in the process. However, it is most economical to operate in a total pressure range that is as low as possible, while maintaining the reactor contents in the liquid phase. The preferred total pressure is in the range of about 400 to about 800 psig. The process weight hourly space velocity is chosen to provide the desired level of ethylbenzene conversion at the chosen reactor temperature and pressure and is typically in the range of about 1 to about 60 hr$^{-1}$. Preferred space velocities are in the range of from about 1 to about 40 hr$^{-1}$, with the more preferred range being from about 1 to about 12 hr$^{-1}$.

Hydrogen may be used in the process, up to the level at which it is soluble in the feed. This amount varies with temperature and pressure, and also with the composition of the feedstock. It is believed that the addition of hydrogen may lead to a lower rate of catalyst deactivation. However, since hydrogen is expensive, its use increases process utilities costs, so that the preferred operation is without the use of hydrogen.

The catalyst compositions of the instant invention are demonstrably superior for liquid-phase isomerization in both overall selectivity (% ethylbenzene conversion divided by % xylene loss) and deactivation rate compared to commercial catalyst compositions. In the liquid phase, overall selectivities of these gallium-containing catalyst compositions can be about 8 or 9 or higher and deactivation rates can be half or less than the rates shown by crystalline borosilicate molecular sieve catalyst compositions.

The following Examples will serve to illustrate certain specific embodiments of the herein disclosed invention. These Examples should not, however, be construed as limiting the scope of the novel invention contained herein as there are many variations which may be made thereon without departing from the spirit of the disclosed invention, as those of skill in the art will recognize.

EXAMPLES

The deactivation rates were calculated as follows:

$$E = \frac{\ln(1 - C^o_{EB}/100)}{\ln(1 - C^t_{EB}/100)}$$

Where $C^o_{EB}$ and $C^t_{EB}$ are the % EB conversions at the beginning and the end of the time period used.

$$T_o = \frac{1}{(1/T_t - \ln E/26534)}$$

Where $T_t$ is the reactor temperature in °R.

Deactivation rate (°F./day) $= \dfrac{T_o - T_t}{D_t - D_o}$

Where $D_t$ and $D_o$ are the days-on-stream at the end and the beginning of the time period used.

Use of the above method assumes that reactor temperature and WHSV are constant throughout the time period used to calculate the deactivation rate.

EXAMPLE 1

A 2400 g portion of water was added to 57.95 g gallium nitrate and to this solution was added 116.58 g of 2,4-pentanedione and 105.33 g tetrapropylammonium bromide. Addition of 761.37 g Ludox AS-40 supplied by E. I. DuPont to this solution and 69.19 g sodium hydroxide raised the pH of the resultant mixture to 10.8. This mixture was charged to a 2-liter stainless steel autoclave and allowed to digest at 150° C. under autogenous pressure for 7 days. The solid product was filtered, washed well with distilled water, and dried at 165° C. The dried material was calcined at 538° C. for 12 hr and exchanged twice with an ammonium acetate solution and dried at 165° C.

Analysis of the product for gallium gave a value of 3.63% of gallium by weight. Further analysis yielded a value of 42.5% of silicon by weight and <5ppm Na. The BET surface area was 404 m$^2$/g and the micropore volume was 0.136 cc/g.

The orthorhombic unit cell parameters and volume from XRD are: a=20.106 Å; b=19.921 Å; c=13.403 Å; and V=5368 Å$^3$.

The XRD powder pattern using copper K alpha radiation is set out in full below.

| d (Å) | I | d (Å) | I |
|---|---|---|---|
| 11.1500 | 100 | 3.3323 | 10 |
| 10.0500 | 55 | 3.3038 | 2 |
| 9.7310 | 22 | 3.0512 | 6 |
| 8.9750 | 2 | 2.9881 | 3 |
| 7.4455 | 2 | 2.9681 | 16 |
| 6.7034 | 5 | 2.7331 | 4 |
| 6.3605 | 10 | 2.5093 | 1 |
| 5.9905 | 14 | 2.4845 | 4 |
| 5.7061 | 8 | 2.3933 | 9 |
| 5.5697 | 10 | 2.0107 | 6 |
| 5.0026 | 8 | 1.9928 | 11 |
| 4.6091 | 4 | 1.9557 | 5 |
| 4.3597 | 6 | 1.9157 | 2 |
| 4.2594 | 8 | 1.8729 | 3 |
| 3.8528 | 45 | 1.6712 | 2 |
| 3.8200 | 44 | 1.6606 | 5 |
| 3.7476 | 19 | | |
| 3.7168 | 23 | | |
| 3.6457 | 15 | | |
| 3.4381 | 5 | | |

EXAMPLE 2

A 29.4 g portion of HAMS-1B crystalline borosilicate molecular sieve made according to the teachings of U.S. Pat. No. 4,269,813 and Eur. Appl. 1,587,921 was placed in a quartz tube reactor and dried by heating to 400° C. for 2 hr with a nitrogen flow of 100 ml/min. The reactor was then cooled to 350° C. and the sample was treated with GaCl$_3$ vapor (21.2 g) over a period of 3.7 hr. During this time, the reactor has heated to 460° C. and held for 3.3 hr. After all the GaCl$_3$ had passed through the reactor, the reactor was cooled. An 8.4 g portion of unreacted GaCl$_3$ was recovered from the reactor outlet. The recovered sieve was washed three times with water at 90° C. and then filtered, air dried on the filter, and finally oven dried at 110° C. overnight. The recovered product weighed 27.7 g and contained 4.4 weight percent Ga. It had a surface area of 383 m$^2$/g and a pore volume of 0.139 cc/g. The results of XPS and AEM tests showed that the gallium is uniformly distributed with a surface concentration that is three quarters of the bulk concentration.

The orthorhombic unit cell parameters and volume from XRD are: a=20.062 Å; b=19.929 Å; c=13.400 Å; and V=5358 Å$^3$.

The XRD powder pattern using copper K alpha radiation is set out below.

| d(Å) | I | d (Å) | I |
| --- | --- | --- | --- |
| 11.1400 | 100 | 3.2508 | 1 |
| 10.0300 | 55 | 3.0493 | 6 |
| 9.7260 | 22 | 2.9801 | 11 |
| 8.9600 | 2 | 2.9419 | 3 |
| 7.4393 | 2 | 2.8614 | 1 |
| 6.7077 | 4 | 2.7298 | 2 |
| 6.3624 | 7 | 2.5969 | 3 |
| 5.9844 | 14 | 2.5154 | 2 |
| 5.7087 | 5 | 2.4867 | 3 |
| 5.5727 | 8 | 2.4147 | 2 |
| 5.3674 | 1 | 2.3910 | 5 |
| 5.1310 | 1 | 2.0085 | 5 |
| 4.9976 | 6 | 1.9930 | 7 |
| 4.6088 | 2 | 1.9578 | 3 |
| 4.3615 | 4 | 1.9134 | 2 |
| 4.2578 | 7 | 1.8714 | 3 |
| 4.0015 | 2 | 1.6699 | 3 |
| 3.8475 | 45 | 1.6592 | 2 |
| 3.8182 | 29 | | |
| 3.7513 | 15 | | |
| 3.7158 | 20 | | |
| 3.6459 | 13 | | |
| 3.4370 | 4 | | |
| 3.3369 | 6 | | |
| 3.3065 | 2 | | |

COMPARATIVE EXAMPLE 3

A catalyst composition comprising 65 weight percent of a ZSM-5 type aluminosilicate molecular sieve made according to the teachings of U.S. Pat. No. 3,702,886 in an alumina binder was tested for liquid-phase xylene isomerization. As shown in Table 3 below, this catalyst composition exhibited an overall selectively (percent ethylbenzene conversion/percent xylene loss) of less than 6.7. The deactivation rate was very high, as evident from the rapid drop in ethylbenzene conversion for the days 5.5–7.5. The deactivation rate was calculated to be 1.5° F. per day in the period 5.5 to 7.5 days.

TABLE 3

Liquid-Phase Xylene Isomerization Using a ZSM-5 Type Aluminosilicate Molecular Sieve

| Time-on-Stream (dys) | Temp (°F.) | Press (psig) | WHSV (hr$^{-1}$) | % EB* Conv. | % Xylene Loss | Overall Selectivity** | PATE*** |
| --- | --- | --- | --- | --- | --- | --- | --- |
| 5.50 | 600 | 400 | 4.96 | 38.82 | 6.54 | 5.94 | 98.66 |
| 6.50 | 600 | 400 | 4.95 | 37.79 | 6.31 | 5.98 | 99.04 |
| 7.50 | 600 | 400 | 4.95 | 36.79 | 6.10 | 6.03 | 99.39 |

*EB is ethylbenzene.
**Overall selectivity is % EB conv. divided by % xylene loss.
***PATE is percent paraxylene approach to equilibrium at the isomerization temperature employed.

COMPARATIVE EXAMPLE 4

A catalyst composition comprising 40 weight percent of a AMS-1B (hydrogen form) crystalline borosilicate molecular sieve made according to the teachings of U.S. Pat. No. 4,269,813 and Eur. Appl. 1,587,921 in an alumina binder was tested for xylene isomerization in the liquid phase. As shown in Table 4 below, this catalyst composition exhibited an overall selectivity of less than 5.3. The deactivation rate for the 14.6th through the 29.6th day on stream was calculated to be 0.19° F.

TABLE 4*

Liquid-Phase Xylene Isomerization Using a HAMS-1B Crystalline Borosilicate Molecular Sieve

| Time-on-Stream (dys) | WHSV (hr$^{-1}$) | % EB Conv. | % Xylene Loss | Overall Selectivity | PATE |
| --- | --- | --- | --- | --- | --- |
| 1.60 | 2.22 | 26.58 | 5.27 | 5.04 | 99.86 |
| 2.60 | 2.21 | 26.77 | 5.31 | 5.05 | 99.94 |
| 4.60 | 2.22 | 26.25 | 5.15 | 5.09 | 100.11 |
| 5.60 | 2. | 26.48 | 5.19 | 5.10 | 100.03 |
| 6.60 | 2.21 | 26.37 | 5.18 | 5.09 | 100.05 |
| 7.60 | 2.22 | 25.51 | 4.95 | 5.15 | 100.12 |
| 8.60 | 2.22 | 25.54 | 4.99 | 5.12 | 99.99 |
| 9.60 | 2.21 | 25.99 | 5.09 | 5.10 | 100.06 |
| 10.60 | 2.21 | 25.87 | 5.06 | 5.11 | 100.07 |
| 11.56 | 2.22 | 25.96 | 5.40 | 4.80 | 100.03 |
| 12.60 | 2.21 | 25.56 | 4.96 | 5.15 | 100.02 |
| 13.60 | 2.22 | 25.60 | 4.98 | 5.14 | 99.86 |
| 14.60 | 2.21 | 25.32 | 4.90 | 5.17 | 100.11 |
| 15.60 | 2.22 | 25.32 | 4.85 | 5.22 | 100.02 |
| 16.60 | 2.23 | 25.01 | 4.81 | 5.20 | 100.04 |
| 17.77 | 2.21 | 24.88 | 4.79 | 5.20 | 100.10 |
| 18.60 | 2.21 | 24.84 | 4.74 | 5.23 | 100.13 |
| 19.60 | 2.21 | 24.65 | 4.71 | 5.24 | 100.08 |
| 20.90 | 2.08 | 26.51 | 5.22 | 5.08 | 100.12 |
| 21.60 | 2.22 | 24.60 | 4.71 | 5.22 | 100.05 |
| 22.60 | 2.22 | 24.40 | 4.65 | 5.24 | 100.09 |
| 23.60 | 2.22 | 24.33 | 4.61 | 5.27 | 100.06 |
| 24.60 | 2.22 | 24.31 | 4.61 | 5.27 | 100.10 |
| 25.60 | 2.22 | 24.25 | 4.62 | 5.25 | 100.08 |
| 26.60 | 2.21 | 24.20 | 4.59 | 5.27 | 100.05 |
| 27.60 | 2.21 | 24.15 | 4.56 | 5.30 | 100.13 |
| 28.60 | 2.21 | 24.04 | 4.57 | 5.26 | 100.10 |
| 29.60 | 2.21 | 23.83 | 4.46 | 5.34 | 100.20 |

*Total pressure was held at 600 psig and temperature at 574–575° F.

EXAMPLE 5

This Example demonstrates the improved performance when a catalyst composition based upon a crystalline molecular sieve containing gallium is used. The catalyst composition of Example 1 comprising 60 weight percent of gallium-containing molecular sieve in a silica matrix was tested for liquid-phase xylene isomerization. As shown in Table 5 below, this catalyst composition exhibited extremely high overall selectively (greater than 9.2) compared to the catalyst compositions tested in Examples 3 and 4. Furthermore, the deactivation rate for the 5.5th through the 14.5th day on stream was calculated to be 0.11° F./day, which is about a factor of two lower than the catalyst composition used in Example 4, and about a factor of 14 lower than that of the catalyst composition used in Example 3.

TABLE 5*

Liquid-Phase Xylene Isomerization Using
Example 1 Gallium Silicate Molecular Sieve

| Time-on-Stream (dys) | WHSV (hr$^{-1}$) | % EB Conv. | % Xylene Loss | Overall Selectivity | PATE |
|---|---|---|---|---|---|
| 3.53 | 2.01 | 18.94 | 2.06 | 9.19 | 100.59 |
| 4.53 | 2.03 | 18.48 | 1.99 | 9.28 | 100.58 |
| 5.53 | 2.00 | 18.35 | 1.95 | 9.40 | 100.65 |
| 6.53 | 2.01 | 18.38 | 1.98 | 9.30 | 100.60 |
| 7.53 | 2.02 | 18.21 | 1.94 | 9.41 | 100.65 |
| 8.53 | 2.02 | 18.30 | 1.95 | 9.40 | 100.62 |
| 9.53 | 2.01 | 18.17 | 1.93 | 9.41 | 100.69 |
| 10.53 | 2.00 | 18.15 | 1.95 | 9.29 | 100.61 |
| 11.53 | 2.01 | 18.06 | 1.93 | 9.36 | 100.68 |
| 12.53 | 2.01 | 18.02 | 1.91 | 9.46 | 100.65 |
| 13.53 | 2.01 | 18.05 | 1.94 | 9.29 | 100.64 |
| 14.53 | 2.01 | 17.98 | 1.93 | 9.31 | 100.63 |

*Total pressure was held at 600 psig and temperature at 605° F.

EXAMPLE 6

This Example demonstrates the improved performance obtained when a catalyst composition (60 weight percent sieve and 40 weight percent silica) based upon a molecular sieve containing gallium made by the method of Example 2 is used for liquid-phase xylene isomerization.

As shown in Table 6 below, this catalyst composition exhibited an overall selectivity greater than 11.9, which is almost a factor of 2 greater than those shown by the catalyst compositions of Examples 3 and 4. The deactivation rate from the 7.5th to 21.5th day on stream was calculated to be 0.10° F./day, which is about a factor of two lower than the HAMS-1B catalyst composition tested in Example 4 and a factor of 15 lower than that for the catalyst composition tested in Example 3.

TABLE 6*

Liquid-Phase Xylene Isomerization Using
Example 2 Gallium Silicate Molecular Sieve

| Time-on-Stream (dys) | WHSV (hr$^{-1}$) | % EB Conv. | % Xylene Loss | Overall Selectivity | PATE |
|---|---|---|---|---|---|
| 0.51 | 2.02 | 15.95 | 1.34 | 11.91 | 99.28 |
| 1.51 | 2.01 | 15.83 | 1.31 | 12.05 | 99.58 |
| 2.51 | 2.01 | 15.77 | 1.30 | 12.11 | 99.47 |
| 3.51 | 2.02 | 15.65 | 1.27 | 12.32 | 99.45 |
| 4.51 | 2.02 | 15.61 | 1.28 | 12.24 | 99.44 |
| 5.51 | 2.01 | 15.52 | 1.26 | 12.36 | 99.52 |
| 6.51 | 2.01 | 15.57 | 1.28 | 12.14 | 99.62 |
| 7.51 | 2.01 | 15.42 | 1.25 | 12.30 | 99.58 |
| 8.51 | 2.01 | 15.52 | 1.27 | 12.25 | 99.53 |
| 9.51 | 2.00 | 15.37 | 1.24 | 12.39 | 99.56 |
| 10.51 | 2.01 | 15.37 | 1.24 | 12.41 | 99.51 |
| 11.51 | 2.02 | 15.36 | 1.25 | 12.30 | 99.52 |
| 12.51 | 2.01 | 15.30 | 1.22 | 12.52 | 99.51 |
| 13.51 | 2.01 | 15.29 | 1.22 | 12.52 | 99.48 |
| 14.51 | 2.02 | 15.29 | 1.24 | 12.32 | 99.41 |
| 15.51 | 2.02 | 15.27 | 1.25 | 12.26 | 99.34 |
| 16.51 | 2.02 | 15.19 | 1.21 | 12.57 | 99.44 |
| 17.51 | 2.02 | 15.12 | 1.22 | 12.38 | 99.49 |
| 18.51 | 2.01 | 15.00 | 1.15 | 13.03 | 99.56 |
| 19.51 | 2.02 | 15.04 | 1.21 | 12.45 | 99.42 |
| 20.51 | 2.01 | 15.04 | 1.20 | 12.54 | 99.44 |
| 21.51 | 2.01 | 14.95 | 1.21 | 12.40 | 99.36 |

*Total pressure was held at 600 psig and temperature at 605° F.

COMPARATIVE EXAMPLE 7

This Example shows that catalyst compositions based on molecular sieves that contain both gallium and aluminum can exhibit better liquid-phase isomerization selectivity than catalyst compositions based on aluminosilicate molecular sieves.

A molecular sieve was prepared in which both a source of gallium (gallium oxide) and a source of aluminum (sodium aluminate) were added to the synthesis gel. The product molecular sieve contained 1.16 wt% aluminum and 2.3 wt% gallium. This molecular sieve was identified as having an MFI framework topology by powder X-ray diffraction. A catalyst composition comprising 65 wt% of the sieve in an alumina matrix was tested for liquid-phase xylene isomerization.

As shown in Table 7 below, this catalyst composition exhibits an overall selectivity greater than 7.6, which is higher than the selectivity exhibited by the catalyst composition of Example 3.

TABLE 7*

Liquid-Phase Xylene Isomerization Using a
Crystalline Molecular Sieve Catalyst Composition
Containing Both Aluminum and Gallium

| Time-on-Stream (dys) | WHSV (hr$^{-1}$) | % EB Conv. | % Xylene Loss | Overall Selectivity | PATE |
|---|---|---|---|---|---|
| 0.52 | 6.26 | 21.25 | 2.79 | 7.62 | 99.58 |
| 1.52 | 6.26 | 18.15 | 2.34 | 7.76 | 99.58 |
| 3.52 | 6.28 | 14.96 | 1.80 | 8.32 | 99.56 |
| 4.52 | 6.34 | 13.86 | 1.67 | 8.32 | 99.52 |
| 5.52 | 6.38 | 12.94 | 1.53 | 8.47 | 99.45 |
| 6.52 | 6.36 | 12.24 | 1.41 | 8.69 | 99.32 |
| 7.52 | 6.28 | 11.69 | 1.39 | 8.42 | 99.00 |
| 8.52 | 6.28 | 11.04 | 1.27 | 8.67 | 98.96 |
| 9.52 | 6.24 | 10.55 | 1.17 | 9.04 | 98.77 |
| 10.52 | 6.24 | 10.10 | 1.13 | 8.96 | 98.58 |
| 11.52 | 6.26 | 9.74 | 1.10 | 8.86 | 98.27 |
| 12.52 | 6.24 | 9.42 | 1.06 | 8.88 | 97.95 |
| 13.52 | 6.26 | 8.66 | 0.95 | 9.15 | 98.05 |
| 14.73 | 6.28 | 8.55 | 0.93 | 9.19 | 97.62 |

*Total pressure was held at 600 psig and temperature at 600° F.

COMPARATIVE EXAMPLE 8

This Example illustrates that the improved overall selectively exhibited by catalyst compositions based on gallium-containing molecular sieves as prepared in Examples 1 and 2 cannot be duplicated by impregnation of a crystalline borosilicate molecular sieve with a gallium compound.

The crystalline borosilicate molecular sieve on alumina catalyst composition of Example 4 was impregnated with a gallium nitrate solution to produce a catalyst composition that contained about 3 weight percent gallium, calculated as the metal. This catalyst composition was used for liquid-phase xylene isomerization.

As shown in Table 8 below, the overall selectivity for the gallium-impregnated sieve on alumina catalyst is in the range of 5.8-6.25. This is only marginally better than the overall selectivity exhibited by the HAMS-1B catalyst composition tested in Example 4.

TABLE 8*

Liquid-Phase Xylene Isomerization Using a
Gallium-Impregnated Crystalline Borosilicate
Molecular Sieve Catalyst Composition

| Time-on-Stream (dys) | WHSV (hr$^{-1}$) | % EB Conv. | % Xylene Loss | Overall Selectivity | PATE |
|---|---|---|---|---|---|
| 3.53 | 2.01 | 18.94 | 2.06 | 9.19 | 100.59 |
| 0.67 | 3.46 | 24.89 | 4.27 | 5.83 | 101.17 |
| 1.67 | 3.43 | 24.94 | 4.24 | 5.83 | 101.21 |
| 2.67 | 3.43 | 24.86 | 4.21 | 5.88 | 101.24 |
| 3.67 | 3.48 | 24.61 | 4.09 | 6.02 | 101.22 |
| 4.67 | 3.48 | 24.61 | 4.08 | 6.03 | 101.17 |
| 5.67 | 3.48 | 24.39 | 4.01 | 6.08 | 101.17 |
| 6.67 | 3.46 | 24.21 | 3.94 | 6.14 | 101.21 |
| 7.67 | 3.48 | 24.41 | 4.05 | 6.03 | 101.21 |
| 8.67 | 3.49 | 24.29 | 3.96 | 6.13 | 101.10 |

TABLE 8*-continued

Liquid-Phase Xylene Isomerization Using a
Gallium-Containing Example 4 Catalyst Composition

| Time-on-Stream (dys) | WHSV (hr$^{-1}$) | % EB Conv. | % Xylene Loss | Overall Selectivity | PATE |
|---|---|---|---|---|---|
| 9.67 | 3.49 | 24.03 | 3.94 | 6.10 | 101.21 |
| 10.67 | 3.47 | 24.04 | 3.94 | 6.10 | 101.28 |
| 11.67 | 3.49 | 24.87 | 3.87 | 6.16 | 101.22 |
| 12.67 | 3.49 | 23.84 | 3.83 | 6.23 | 101.28 |
| 13.67 | 3.50 | 23.64 | 3.82 | 6.18 | 101.13 |
| 14.67 | 3.51 | 23.65 | 3.81 | 6.20 | 101.18 |
| 15.67 | 3.46 | 23.67 | 3.86 | 6.14 | 101.17 |
| 16.67 | 3.48 | 25.42 | 4.30 | 5.91 | 101.31 |
| 17.67 | 3.47 | 25.35 | 4.25 | 5.97 | 101.37 |
| 18.67 | 3.47 | 25.44 | 4.28 | 5.94 | 101.22 |
| 19.67 | 3.43 | 25.35 | 4.24 | 5.99 | 101.33 |
| 20.67 | 3.44 | 25.36 | 4.27 | 5.94 | 101.24 |
| 21.67 | 3.44 | 25.25 | 4.22 | 5.99 | 101.37 |
| 22.67 | 3.42 | 25.33 | 4.24 | 5.95 | 101.29 |
| 23.67 | 3.43 | 25.16 | 4.23 | 5.95 | 101.32 |
| 24.67 | 3.45 | 25.03 | 4.15 | 6.03 | 101.39 |
| 25.67 | 3.44 | 25.13 | 4.22 | 5.96 | 101.31 |
| 26.67 | 3.45 | 24.97 | 4.17 | 5.98 | 101.24 |
| 27.67 | 3.42 | 24.81 | 4.11 | 6.04 | 101.21 |
| 28.67 | 3.47 | 24.78 | 4.11 | 6.03 | 101.22 |
| 29.67 | 3.48 | 24.40 | 4.05 | 6.04 | 101.21 |
| 30.67 | 3.46 | 24.40 | 4.05 | 6.03 | 101.25 |
| 31.67 | 3.49 | 24.36 | 3.99 | 6.11 | 101.33 |
| 32.67 | 3.49 | 24.50 | 4.06 | 6.04 | 101.23 |
| 33.67 | 3.48 | 24.33 | 4.00 | 6.07 | 101.29 |
| 34.67 | 3.49 | 24.09 | 3.98 | 6.05 | 101.33 |
| 35.67 | 3.49 | 24.12 | 3.96 | 6.09 | 101.23 |
| 36.67 | 3.47 | 24.08 | 3.95 | 6.09 | 101.22 |
| 37.67 | 3.44 | 23.94 | 3.88 | 6.16 | 101.36 |
| 38.67 | 3.49 | 23.80 | 3.86 | 6.16 | 101.35 |
| 39.67 | 3.50 | 23.69 | 3.82 | 6.21 | 101.24 |

*Total pressure was held at 600 psig and temperature at 600–604° F.

What is claimed is:

1. In a process to catalytically isomerize in the liquid phase a stream containing a major amount of one or more xylenes and a minor amount of ethylbenzene to a product rich in paraxylene, the improvement comprising isomerizing said stream under isomerization conditions over a catalyst composition which contains about 10 to about 80 weight percent, based upon the total weight of said catalyst composition, of a gallium-containing, crystalline silicate molecular sieve incorporated into about 20 to about 90 weight percent, based upon the total weight of said catalyst composition, of a n amorphous silica matrix, said sieve containing about 0.5 to about eight weight percent gallium, calculated as the metal, substantially all of said gallium occupying molecular sieve lattice positions or intimately associated with the crystal lattice of said crystalline silicate molecular sieve.

2. In a process to catalytically isomerize in the liquid phase a stream containing a major amount of one or more xylenes and a minor amount of ethylbenzene to a product rich in paraxylene, the improvement comprising isomerizing said stream under isomerization conditions over a catalyst composition which contains about 10 to about 80 weight percent, based upon the total weight of said catalyst composition, of a gallium-containing, crystalline silicate molecular sieve incorporated into about 20 to about 90 weight percent, based upon the total weight of said catalyst composition, of a n amorphous silica matrix, said sieve containing about 0.5 to about eight weight percent gallium, calculated as the metal, substantially all of said gallium occupying molecular sieve lattice positions or intimately associated with the crystal lattice of said crystalline silicate molecular sieve, and said sieve providing an x-ray pattern comprising the following x-ray diffraction lines and strengths:

| Interplanar Spacing d, Å | Assigned Strength | Interplanar Spacing d, Å | Assigned Strength |
|---|---|---|---|
| 11.14 ± 0.5 | VS | 3.82 ± 0.1 | M |
| 10.05 ± 0.4 | S | 3.75 ± 0.1 | W |
| 6.36 ± 0.2 | W | 3.72 ± 0.1 | M |
| 5.99 ± 0.15 | W | 3.64 ± 0.1 | W |
| 5.57 ± 0.15 | W | 33.4 ± 0.05 | W |
| 3.85 ± 0.1 | S | 2.98 ± 0.04 | W |

3. The process of claim 2 wherein said gallium-containing crystalline silicate molecular sieve contains between about one and about eight weight percent gallium.

4. The process of claim 3 wherein said catalyst composition contains between about thirty and sixty-five weight percent of said gallium-containing crystalline silicate molecular sieve.

5. The process of claim 2 wherein said gallium-containing, crystalline silicate molecular sieve is made by combining a source of gallium ions, a source of silica, and tetrapropylammonium bromide as a template compound in an aqueous solution having a pH between about 9 and about 12 for between about two and twenty days under hydrothermal conditions at a temperature of about 125° C. to about 200° C. and separating, drying and calcining the solid gallium-containing, crystalline silicate molecular sieve product.

6. The process of claim 2 wherein said gallium-containing, crystalline, silicate molecular sieve is made by treating at elevated temperature a HAMS-1B crystalline borosilicate molecular sieve with a volatile gallium compound in the vapor phase until substantially all of the boron is removed and at least some of the gallium occupies molecular sieve lattice positions or is intimately associated with the crystal lattice of said crystalline silicate molecular sieve.

* * * * *